United States Patent
Yoshida et al.

(10) Patent No.: US 9,844,570 B2
(45) Date of Patent: Dec. 19, 2017

(54) PLURIPOTENT STEM CELL THAT INDUCES REPAIR AND REGENERATION AFTER MYOCARDIAL INFARCTION

(71) Applicants: CLIO, INC., Akita (JP); GIFU UNIVERSITY, Gifu (JP); TOHOKU UNIVERSITY, Miyagi (JP)

(72) Inventors: Masanori Yoshida, Akita (JP); Shinya Minatoguchi, Gifu (JP); Mari Dezawa, Miyagi (JP)

(73) Assignees: CLIO, INC., Akita (JP); GIFU UNIVERSITY, Gifu (JP); TOHOKU UNIVERSITY, Miyagi (JP)

( * ) Notice: Subject to any disclaimer, the term of this patent is extended or adjusted under 35 U.S.C. 154(b) by 0 days.

(21) Appl. No.: 14/421,754

(22) PCT Filed: Aug. 15, 2013

(86) PCT No.: PCT/JP2013/071981
§ 371 (c)(1),
(2) Date: Feb. 13, 2015

(87) PCT Pub. No.: WO2014/027684
PCT Pub. Date: Feb. 20, 2014

(65) Prior Publication Data
US 2015/0196600 A1 Jul. 16, 2015

(30) Foreign Application Priority Data

Aug. 17, 2012 (JP) .................................. 2012-181029
Feb. 19, 2013 (WO) .................. PCT/JP2013/054049

(51) Int. Cl.
A61K 48/00 (2006.01)
A61K 35/28 (2015.01)
C12N 5/074 (2010.01)

(52) U.S. Cl.
CPC ............ *A61K 35/28* (2013.01); *C12N 5/0607* (2013.01)

(58) Field of Classification Search
CPC ................................ A61K 35/28; C12N 5/067
See application file for complete search history.

(56) References Cited

U.S. PATENT DOCUMENTS 5,827,735 A * 10/1998 Young .................... C07K 14/52
435/325
2009/0053277 A1 2/2009 Nagaya et al.
2011/0274663 A1 11/2011 Shirono et al.
2012/0094380 A1 4/2012 Shih et al.

FOREIGN PATENT DOCUMENTS

| JP | 2002511094 A | 4/2002 |
|---|---|---|
| JP | 2002521493 A | 7/2002 |
| JP | 2010-246476 A | 12/2010 |
| KR | 10-2010-0010951 A | 2/2010 |
| WO | 02/057430 A2 | 7/2002 |
| WO | 03/006950 A2 | 1/2003 |
| WO | 2006/080434 A1 | 8/2006 |
| WO | 2009/046058 A1 | 4/2009 |
| WO | 2009/057537 A1 | 7/2009 |
| WO | 2011/007900 A1 | 1/2011 |

OTHER PUBLICATIONS

Kuroda et al. Biol. Pharm Bull 36(2):189-192, 2012.*
Shake et al. Ann Thorac Surg 73:1919-126, 2002.*
International Search Report corresponding to PCT/JP2013/071981 dated Oct. 29, 2013, 2 pages.
Kuroda, Yasumasa et al., "Unique multipotent cells in adult human mesenchymal cell populations" (May 11, 2010), PNAS 107(19):8639-8643.
Katritsis et al., "Transcoronary Transplantation of Autologous Mesenchymal Stem Cells and Endothelial Progenitors Into Infarcted Human Myocardium," Catheterization and Cardiovascular Interventions, Jun. 13, 2005, vol. 65, pp. 321-329.
Kagaku Kenkyu-Hi et al., "Detection of VSEL cells in umbilical cord blood and development of co-culture system with umbilical cord-derived mesenchymal stem cells," Jun. 5, 2012, retrieved on Dec. 22, 2015, at <URL:https://kaken.nii.ac.jp/pdf/2011/seika/C-19/12601/21659069seika.pdf.>.
News Medical, "Effectiveness of VSEL stem cells in regenerative medicine demonstrated at the ASH meeting", Dec. 21, 2009, retrieved on Dec. 21, 2015, at: <URL: http://www.news-medical.net/news/20091221/Effectiveness-of-VSEL-stem-cells-in-regenerative-medicine-demonstrated-at-the-ASH-meeting.aspx.>.
Malecki et al., "Anchoring stem cells to the sites o fthe ischemic heart injury with the polyspecific antibodies," Protein Science, vol. 21, No. S1, Aug. 2012, pp. 160-161, Abstract.
McKeown, S., "Definining normoxia, physixia and hypoxia in tumours—implications for treatment response," Br J Radiol, 87:20130676, 2014.
SIGMA-ALDRICH®, Dulbecco's Modified Eagle's Medium—low glucose, retrieved online at <http://www.sigmaaldrich.com/catalog/product/sigma/d6046?lang=en&region=US> on Mar. 1, 2017, 4 pages.

* cited by examiner

*Primary Examiner* — Marcia S Noble
(74) *Attorney, Agent, or Firm* — Kilpatrick Townsend & Stockton LLP

(57) ABSTRACT

An object of the present invention is to provide a novel medical application for use in regenerative medicine that uses pluripotent stem cells (Muse cells). The present invention provides a cell preparation for treating myocardial infarction, and particularly serious massive myocardial infarction and heart failure associated therewith, that contains pluripotent stem cells positive for SSEA-3 isolated from biological mesenchymal tissue or cultured mesenchymal cells. The cell preparation of the present invention is based on a cardiac tissue regeneration mechanism by which Muse cells are made to selectively accumulate in damaged myocardial tissue and differentiate into cardiac muscle in that tissue as a result of intravenous administration of Muse cells to a subject presenting with the aforementioned disorders.

13 Claims, 9 Drawing Sheets

PLURIPOTENT STEM CELL THAT INDUCES REPAIR AND REGENERATION AFTER MYOCARDIAL INFARCTION

TECHNICAL FIELD

The present invention relates to a cell preparation used in regenerative medicine. More particularly, the present invention relates to a cell preparation containing pluripotent stem cells that are effective for repairing and regenerating cardiac tissue that has been damaged by myocardial infarction.

BACKGROUND ART

Myocardial infarction, which is caused by myocardial necrosis brought about by coronary artery occlusion, is an important issue to be solved in clinical medicine since it causes sudden cardiac death and chronic cardiac death. In the case of acute myocardial infarction in particular, the mortality rate is high at 35% to 50%, and 60% to 70% of fatal cases die within 1 to 2 hours after the attack. In addition, even if patients survive the acute stage, in cases in which the myocardial necrotic lesion is large following the initial attack, there is a high risk of succumbing to recurrent myocardial infarction or accompanying heart failure. Thus, in treating myocardial infarction, it is necessary to rapidly implement treatment soon after the attack has occurred, and it is important to minimize the size of the necrotized myocardium, namely the infarct size, as much as possible.

For example, in myocardial infarctions such as severe massive myocardial infarction, since left ventricular remodeling proceeds leading to heart failure, prognosis is known to be poor. In general, coronary recanalization therapy in the form of thrombolytic therapy or revascularization is typically performed for myocardial infarction. However, there are many cases in which the effects of recanalization may not be obtained or conversely, myocardial cells may be damaged by reperfusion injury and the like, and satisfactory therapeutic effects may not be obtained by recanalization therapy alone. Consequently, although studies have been conducted on pharmaceutical agents expected to demonstrate myocardial protective action for use as an adjuvant therapy to recanalization therapy, a satisfactory pharmaceutical agent has yet to be found. In addition, in the case of serious massive myocardial infarction, prognosis would improve if it were possible to regenerate necrotic myocardial tissue and improve left ventricular remodeling. However, there is currently no medical treatment that is effective against the aforementioned disorders.

As was previously described, in the treatment of myocardial infarction, although it is required to rapidly provide treatment soon after an attack, since there is no definitive treatment method for minimizing infarct size, efforts are being focused on regenerating the myocardial tissue that has necrotized. In particular, attention has recently been focused on biological cells capable of contributing to tissue regeneration. Although known examples of cells obtained from adults that have the ability to differentiate include mesenchymal stem cells (MSC) that have the ability to differentiate into bone, cartilage, adipocytes, neurons or skeletal muscle and the like (Non-Patent Documents 1 and 2), these consist of cell groups containing various cells, the actual state of their ability to differentiate is not understood, and there have been considerable fluctuations in therapeutic effects. In addition, although iPS cells (Patent Document 1) have been reported to be adult-derived pluripotent stem cells, in addition to the establishment of iPS cells requiring an extremely complex procedure involving the introduction of specific genes into mesenchymal cells in the form of a skin fibroblast fraction and the introduction of specific compounds into somatic cells, since iPS cells have a high tumorigenic potential, extremely high hurdles must be overcome for their clinical application.

It has been determined from research by M. Dezawa, one of the inventors of the present invention, that multilineage-differentiating stress enduring cells (Muse cells) expressing surface antigen in the form of stage-specific embryonic antigen-3 (SSEA-3), which are present in mesenchymal cell fractions and can be obtained without going through an induction procedure, are responsible for the pluripotency possessed by mesenchymal cell fractions, and that they have the potential for application to disease treatment aimed at tissue regeneration. In addition, Muse cells were also determined to be able to be concentrated by stimulating mesenchymal cell fractions with various types of stress (Patent Document 2, Patent Document 3). However, there have yet to be any examples of the use of Muse cells for the prevention and/or treatment of myocardial infarction such as serious massive myocardial infarction or its accompanying heart failure, and the obtaining of anticipated therapeutic effects has yet to be clearly determined.

PRIOR ART DOCUMENTS

Patent Documents

[Patent Document 1] Japanese Patent No. 4183742
[Patent Document 2] International Publication No. WO 2011/007900

Non-Patent Documents

[Non-Patent Document 1] Dezawa, M., et al., J. Clin. Invest., Vol. 113, p. 1701-1710 (2004)
[Non-Patent Document 2] Dezawa, M., et al., Science, Vol. 309, p. 314-317 (2005)
[Non-Patent Document 3] Wakao, S., et al., Proc. Natl. Acad. Sci. USA, Vol. 108, p. 9875-9880 (2011)

DISCLOSURE OF THE INVENTION

Problems to be Solved by the Invention

An object of the present invention is to provide a novel therapeutic application using pluripotent stem cells (Muse cells) in regenerative medicine. More specifically, an object of the present invention is to provide a cell preparation for the treatment of myocardial infarction (and particularly, serious massive myocardial infarction), as well as the prevention and/or treatment of its accompanying heart failure, that contains Muse cells.

Means for Solving the Problems

The inventors of the present invention found that, by administering Muse cells by intravenous injection for myocardial infarction induced by coronary artery ischemia (30 minutes) using Japanese white rabbits, the Muse cells accumulate locally in damaged myocardial tissue, differentiate into myocardial cells within the damaged myocardial tissue, and bring about a reduction in infarct size and improvement or restoration of cardiac function, thereby leading to completion of the present invention.

Namely, the present invention is as described below.

[1] A cell preparation for treating myocardial infarction, containing pluripotent stem cells positive for SSEA-3 isolated from biological mesenchymal tissue or cultured mesenchymal cells.

[2] The cell preparation described in [1], wherein the pluripotent stem cells positive for SSEA-3 contain a concentrated cell fraction as a result of stimulation by external stress.

[3] The cell preparation described in [1] or [2] above for prevention and/or treatment of heart failure following serious massive myocardial infarction in humans.

[4] The cell preparation described in [1] to [3] above, wherein the pluripotent stem cells are CD105-positive.

[5] The cell preparation described in [1] to [4] above, wherein the pluripotent stem cells are CD117-negative and CD146-negative.

[6] The cell preparation described in [1] to [5] above, wherein the pluripotent stem cells are CD117-negative, CD146-negative, NG2-negative, CD34-negative, vWF-negative and CD271-negative.

[7] The cell preparation described in [1] to [6] above, wherein the pluripotent stem cells are CD34-negative, CD117-negative, CD146-negative, CD271-negative, NG2-negative, vWF-negative, Sox10-negative, Snail-negative, Slug-negative, Tyrp1-negative and Dct-negative.

[8] The cell preparation described in [1] to [7], wherein the pluripotent stem cells are pluripotent stem cells having all of the properties indicated below:
(i) low or absent telomerase activity;
(ii) ability to differentiate into any of the three germ layers;
(iii) absence of demonstration of neoplastic proliferation; and,
(iv) self-renewal ability.

[9] The cell preparation described in [1] to [8] above, wherein the pluripotent stem cells have the ability to accumulate at the site of myocardial infarction.

[10] The cell preparation described in [1] to [9] above, wherein the pluripotent stem cells have the ability to differentiate into vascular endothelial cells.

[11] The cell preparation described in [1] to [9] above, wherein the pluripotent stem cells have the ability to differentiate into myocardial cells.

[12] The cell preparation described in [1] to [11] above, wherein the pluripotent stem cells are administered into a vein or coronary artery of a subject within 1 month after ischemia one to ten times in a therapeutically effective amount of $1\times10^3$ cells/individual to $1\times10^6$ cells/individual.

[13] The cell preparation described in [1] to [12] above, wherein the size of the myocardial infarct is reduced in comparison with a non-administered control.

[14] The cell preparation described in [1] to [13] above, wherein at least one cardiac function indicator, selected from the group consisting of change in left ventricular pressure over time, left ventricular end-diastolic dimension (LVDd), ejection fraction (EF), left ventricular fractional shortening (FS) and left ventricular end-systolic dimension (LVDs), is restored to the normal value.

EFFECTS OF THE INVENTION

The present invention is able to dramatically reduce the size of a myocardial infarct by means of a cardiac tissue regeneration mechanism by which Muse cells are made to selectively accumulate in damaged myocardial tissue and differentiate into cardiac muscle following their administration into a vein or the like of a subject suffering from myocardial infarction, and particularly serious massive myocardial infarction.

BRIEF DESCRIPTION OF THE DRAWINGS

FIG. 9 depicts photographs of one sample randomly selected from each transplant group corresponding to the results shown in FIG. 8.

MODE FOR CARRYING OUT THE INVENTION

Figure 1:
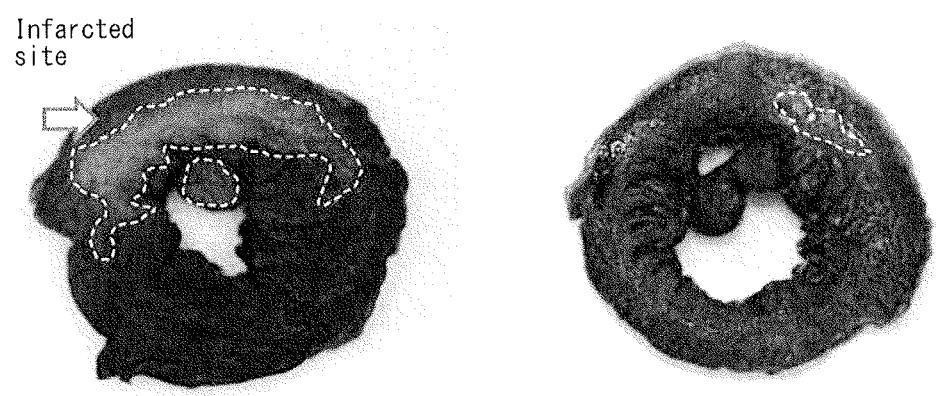
FIG. 1 depicts sections of cardiac tissue containing an infarcted site obtained from a rabbit model of myocardial infarction. The infarcted sites were determined by triphenyl tetrazolium chloride (TTC) staining. The non-stained regions surrounded by broken lines indicate the infarcted sites. The right panel is a tissue section obtained 14 days after reperfusion that was reperfused 30 minutes after ischemia followed by intravenous administration of Muse cells 24 hours after reperfusion. The left panel is a tissue section in which physiological saline was administered intravenously instead of Muse cells. Transplantation of Muse cells resulted in a significant decrease in the size of the infarcted site.

The present invention relates to a cell preparation for treating myocardial infarction that contains SSEA-3-positive pluripotent stem cells (Muse cells). The following provides a detailed explanation of the present invention.

1. Applicable Diseases

The present invention is used for the purpose of treating myocardial infarction, and particularly serious massive myocardial infarction, along with its accompanying heart failure, using a cell preparation containing SSEA-3-positive pluripotent stem cells (Muse cells). Here, "myocardial infarction" refers to myocardial necrosis brought about by coronary artery occlusion. In addition, "heart failure" refers to a syndrome caused by the failure of cardiac function to circulate an adequate amount of blood, and includes a decrease in cardiac output and an accompanying increase in venous pressure as well as various clinical symptoms occurring as a result thereof. Myocardial infarction is a cause of sudden cardiac death and chronic cardiac death. In the case of acute myocardial infarction in particular, the mortality rate is high at 35% to 50%, and 60% to 70% of fatal cases die within 1 to 2 hours after the attack. In addition, even if patients survive the acute stage, in cases in which the myocardial necrotic lesion is large following the initial attack, there is a high risk of succumbing to recurrent myocardial infarction. Thus, in treating myocardial infarction, it is necessary to rapidly implement treatment soon after the attack has occurred, and it is important to minimize the size of the necrotized myocardium, namely the infarct size, as much as possible. In addition, various classifications are used to assess the severity of myocardial infarction. Examples thereof include classification according to the amount of elapsed time, morphological classification (range within the myocardium, site, and/or size of necrosis, etc.), form of myocardial necrosis, post-infarction ventricular remodeling, hemodynamic classification (as related to treatment, prevention and the like) and classification according to clinical severity. Here, myocardial infarction having a high degree of severity in which myocardial necrosis covers a wide range in particular is referred to as "severe massive myocardial infarction". An example thereof is complete occlusion of the distal portion of the left coronary artery. In addition, severe massive myocardial infarction is known to be associated with a poor prognosis since left ventricular remodeling of cardiac muscle proceeds resulting in heart failure. Here, "left ventricular remodeling" following myocardial infarction refers to a series of changes, including hypertrophy of myocardial cells, increased interstitium (extracellular matrix) and enlargement of the cardiac lumen, that occur compensatory to decreased cardiac function caused by thinning of the infarcted site that occurs following myocardial infarction. Since long-term prognosis following myocardial infarction is correlated with the degree of left ventricular dysfunction, inhibition of left ventricular remodeling is essential for maintaining and preserving the function of the left ventricle.

In general, in the case of myocardial infarction within 6 hours of attack, aggressive reperfusion therapy of the occluded coronary artery makes it possible to reduce the necrotized range of cardiac muscle. In addition to this therapy, it is meaningful to perform reperfusion therapy in cases in which 24 hours or less have elapsed since attack. In the case of the acute stage, coronary artery disease is frequently treated using a catheter. In contrast, the cell preparation of the present invention can be targeted for treatment of cases in which the amount of time until reperfusion is extremely long or cases in which reperfusion and catheterization were ineffective. In other words, according to the present invention, a cell preparation containing Muse cells is provided for the purpose of treating myocardial infarction based on regeneration of cardiac tissue, including prevention of the occurrence of heart failure caused by left ventricular remodeling.

2. Cell Preparation (1) Pluripotent Stem Cells (Muse Cells)

The existence of the pluripotent stem cells used in the cell preparation of the present invention in the body was discovered by M. Dezawa, one of the applicants of the present invention, and the cells were named "multilineage-differentiating stress enduring (Muse) cells". Muse cells can be obtained from bone marrow aspirates or skin tissue such as dermal connective tissue, and are sporadically present in the connective tissue of various organs. In addition, these cells have both the properties of pluripotent stem cells and mesenchymal stem cells, and are identified as being double-positive for each of the cell surface markers of "stage-specific embryonic antigen-3 (SSEA-3)" and "CD105". Thus, Muse cells or cell populations containing Muse cells can be isolated from body tissue by using these antigen markers as indicators. In addition, since Muse cells are resistant to stress, they can be concentrated from biological mesenchymal tissue or cultured mesenchymal cells by stimulating with various types of stress. A cell fraction in which Muse cells have been concentrated by stress stimulation can also be used for the cell preparation of the present invention. Details regarding methods used to isolate, identify and concentrate Muse cells as well as their characteristics are disclosed in International Publication No. WO 2011/007900. In addition, as has been reported by Wakao, et al. (2011, previously cited), in the case of using a cell culture obtained by culturing mesenchymal cells present in bone marrow, skin and the like as the parent population of Muse cells, all cells positive for SSEA-3 are known to be positive for CD105. Thus, in the cell preparation of the present invention, in the case of isolating Muse cells from biological mesenchymal tissue or cultured mesenchymal cells, Muse cells can be purified and used simply by using SSEA-3 as an antigen marker. Furthermore, in the present description, pluripotent stem cells (Muse cells) able to be used in a cell preparation for treating myocardial infarction that have been isolated from biological mesenchymal tissue or cultured mesenchymal cells by using SSEA-3 as an antigen marker, or a cell population containing Muse cells, may simply be described as "SSEA-3-positive cells".

Simply speaking, Muse cells or cell populations containing Muse cells can be isolated from biological tissue (such as mesenchymal tissue) using antibody to the cell surface marker SSEA-3 alone or using antibody to SSEA-3 and CD105, respectively. Here, "biological tissue" refers to the biological tissue of a mammal. In the present invention, although an embryo in a development stage prior to a fertilized egg or blastula stage is not included in biological tissue, an embryo in a development stage in or after the fetus or blastula stage, including the blastula, is included. Examples of mammals include, but are not limited to, primates such as humans or monkeys, rodents such as mice, rats, rabbits or guinea pigs as well as cats, dogs, sheep, pigs, cows, horses, donkeys, goats and ferrets. The Muse cells used in the cell preparation of the present invention are clearly distinguished from embryonic stem (ES) cells and embryonic germ (EG) cells in that they are derived from biological tissue. In addition, "mesenchymal tissue" refers to tissue of bone, cartilage, fat, blood, bone marrow, skeletal muscle, dermis, ligaments, tendons or heart and the like, as well as connective tissue thereof. For example, Muse cells can be obtained from bone marrow and skin. In addition, an object of the present invention is to provide a cell preparation used for the purpose of regenerating cardiac muscle, and for example, Muse cells are preferably used that have been isolated from mesenchymal tissue collected from the living body. In addition, Muse cells may also be isolated from cultured mesenchymal cells using the aforementioned isolation means. Furthermore, Muse cells used in the cell preparation of the present invention may be autologous or allogenic relative to the recipient who receives the cell transplant.

As has been described above, although Muse cells or cell populations containing Muse cells can be isolated from biological tissue by using their property of being SSEA-3-positive and CD105-positive, human adult skin is known to contain various types of stem cells and precursor cells. However, Muse cells are not the same as these cells. Examples of such stem cells and precursor cells include skin-derived precursor (SKP) cells, neural crest stem cells (NCSC), melanoblasts (MB), perivascular cells (PC), endothelial precursor (EP) cells and adipose-derived stem cells (ADSC). Muse cells can be isolated from these cells by using "non-expression" of a unique marker as an indicator of these cells. More specifically, Muse cells can be isolated by using non-expression of at least one of 11 markers, such as 1, 2, 3, 4, 5, 6, 7, 8, 9, 10 or 11 markers, selected from the group consisting of CD34 (marker for EP and ADSC), CD117 (c-kit) (MB marker), CD146 (PC and ADSC marker), CD271 (NGFR) (NCSC marker), NG2 (PC marker), vWF factor (von Willebrand factor) (EP marker), Sox10 (NCSC marker), Snail (SKP marker), Slug (SKP marker), Tyrp1 (MB marker) and Dct (MB marker). For example, although not limited thereto, Muse cells can be isolated by using non-expression of CD117 and CD146 as an indicator, can be isolated using non-expression of CD117, CD146, NG2, CD34, vWF and CD271 as an indicator, and can be isolated by using non-expression of the aforementioned 11 markers as an indicator.

In addition, Muse cells having the aforementioned characteristics used in the cell preparation of the present invention may have at least one property selected from the group consisting of:

(i) low or absent telomerase activity;

(ii) ability to differentiate into any of the three germ layers;

(iii) absence of demonstration of neoplastic proliferation; and, (iv) self-renewal ability.

In one aspect of the present invention, the Muse cells used in the cell preparation of the present invention have all of the aforementioned properties. Here, with respect to the aforementioned (i), "low or absent telomerase activity" refers to telomerase activity being low or being unable to be detected in the case of having detected telomerase activity using, for example, the Trapeze XL Telomerase Detection Kit (Millipore Corp.). "Low" telomerase activity refers to having telomerase activity roughly equal to that of human fibroblasts, for example, or having telomerase activity that is $\frac{1}{5}$ or less and preferably $\frac{1}{10}$ or less in comparison with Hela cells. With respect to the aforementioned (ii), Muse cells have the ability to differentiate into the three germ layers (endoderm, mesoderm and ectoderm) in vitro and in vivo, and by inducing to differentiate by culturing in vitro, for example, can differentiate into skin, liver, nerve, muscle, bone or fat and the like. In addition, Muse cells may also demonstrate the ability to differentiate into the three germ layers in the case of transplanting in vivo into testes, for example. Moreover, Muse cells also have the ability to migrate, graft and differentiate into a damaged organ (such as the heart, skin, spinal cord, liver or muscle) by being transplanted into the body by intravenous injection. With respect to the aforementioned (iii), although Muse cells proliferate at a growth rate of about 1.3 days in a suspension culture, they also have the property of discontinuing proliferation for about 10 days, and in the case of having been transplanted into testes, have the property of not becoming malignant for at least six months. In addition, with respect to the aforementioned (iv), Muse cells have self-renewal (self-replication) ability. Here, "self-renewal" refers to culturing cells contained in an embryoid body-like cell mass obtained by suspension culturing single Muse cell and allowing them to reform an embryoid body-like cell mass. Self-renewal may be carried out for one cycle or repeated for a plurality of cycles.

In addition, a cell fraction containing Muse cells used in the cell preparation of the present invention may be a cell fraction obtained by a method consisting of applying an external stress stimulus to biological mesenchymal tissue or cultured mesenchymal cells, eradicating those cells other than cells that are resistant to the external stress, and recovering the surviving cells, in which SSEA-3-positive and CD105-positive pluripotent stem cells having all of the properties indicated below have been concentrated:

(i) SSEA-3 positive;
(ii) CD105-positive;
(iii) low or absent telomerase activity;
(iv) ability to differentiate into three germ layers;
(v) absence of demonstration of neoplastic proliferation; and,
(vi) self-renewal ability.

The aforementioned external stress may consist of any of protease treatment, culturing at a low oxygen concentration, culturing under phosphate-deficient conditions, culturing under serum-deficient conditions, culturing under poor nutritional conditions, culturing under exposure to heat shock, culturing under mechanical stimulation, culturing under shaking treatment, culturing under pressure treatment and physical shock or a combination of a plurality thereof.

The duration of the aforementioned protease treatment in order to impart external stress to cells is preferably a total of 0.5 hours to 36 hours. In addition, the protease concentration is the concentration used when exfoliating cells that have adhered to the culture vessel, when breaking up a cell mass into single cells, or when recovering single cells from tissue.

The aforementioned protease is preferably a serine protease, aspartic acid protease, cysteine protease, metalloprotease, glutamic acid protease or N-terminal threonine protease. The aforementioned protease is more preferably trypsin, collagenase or dispase.

In addition, Muse cells having the aforementioned characteristics used in the cell preparation of the present invention accumulate in damaged myocardial tissue (site of myocardial infarction) following intravenous administration as will be subsequently described, and as a result of differentiating into myocardial cells in that tissue, are able to reduce infarct size and enable cardiac function to improve or return to normal (Examples 2 to 4).

(2) Preparation and Use of Cell Preparation

The cell preparation of the present invention, although not limited thereto, is obtained by suspending Muse cells or a cell population containing Muse cells obtained in the aforementioned (1) in physiological saline or a suitable buffer (such as phosphate-buffered physiological saline). In this case, in the case the number of Muse cells isolated from autologous or allogenic tissue is low, cells may be cultured prior to cell transplant and allowed to proliferate until a prescribed cell concentration is obtained. Furthermore, as has been previously reported (International Publication No. WO 2011/007900), since Muse cells do not undergo neoplastic transformation, there is little likelihood of the cells becoming malignant even if cells recovered from biological tissue are contained that have still not differentiated, thereby making them safe. In addition, although there are no particular limitations thereon, culturing of recovered Muse cells can be carried out in an ordinary growth medium (such as minimum essential medium-α (α-MEM) containing 10% bovine calf serum). More specifically, a solution containing a prescribed concentration of Muse cells can be prepared by selecting media, additives (such as antibiotics and serum) and the like suitable for the culturing and proliferation of Muse cells with reference to the aforementioned International Publication No. WO 2011/007900. In the case of administering the cell preparation of the present invention for treatment of myocardial infarction to a human, roughly several milliliters of bone marrow aspirate are collected from human ilium, and after isolating Muse cells by using an antigen marker for SSEA-3 as an indicator, the cells are allowed to proliferate by culturing for an appropriate amount of time until an effective therapeutic dose is reached (such as for 2 to 3 weeks), followed by preparing autologous Muse cells in the form of a cell preparation.

In addition, when using the cell preparation of Muse cells, dimethylsulfoxide (DMSO) or serum albumin for protecting the cells, or antibiotics and the like for preventing contamination and growth of bacteria, may also be contained in the cell preparation. Moreover, other pharmaceutically allowable components (such as a carrier, vehicle, disintegrating agent, buffer, emulsifier, suspending agent, soothing agent, stabilizer, storage agent, preservative or physiological saline), or cells or components other than Muse cells contained in mesenchymal cells, may also be contained in the cell preparation. A person with ordinary skill in the art is able to add these factors and pharmaceutical agents to a cell preparation at suitable concentrations. In this manner, Muse cells can be used in the form of a pharmaceutical composition containing various types of additives.

The number of Muse cells contained in the cell preparation prepared in the manner described above can be suitably adjusted in consideration of the gender, age and body weight of the subject, disease state and state in which the cells are used so as to obtain the desired effect in treatment of myocardial infarction (such as reduction of infarct size or improvement of cardiac function). In Examples 1 to 4 to be subsequently described, although a rabbit model of myocardial infarction was produced and various types of effects of transplanting Muse cells were examined, extremely superior effects were obtained by administering SSEA3-positive cells to Japanese white rabbits weighing about 2 kg to 3 kg at $5 \times 10^5$ cells/animal. On the basis of this result, superior effects can be expected to be obtained by administering $1.7 \times 10^5$ to $2.5 \times 10^5$ cells/kg per individual mammal based on body weight. On the other hand, SSEA-3-positive cells may be contained in a cell preparation at $1 \times 10^6$ cells/individual or less, for example, as the amount per single administration in order to prevent vascular occlusion attributable to administration of cells. Here, examples of individuals include, but are not limited to, rabbits and humans. In addition, the cell preparation of the present invention may be administered a plurality of times (such as 2 to 10 times) at a suitable interval (such as twice per day, once per day, twice per week, once per week or once every two weeks) until the desired therapeutic effect is obtained. Thus, although dependent upon the status of the subject, the therapeutically effective dose is preferably administered, for example, 1 to 10 times at $1 \times 10^3$ cells to $1 \times 10^6$ cells per individual. Although there are no particular limitations thereon, examples of total individual doses include $1 \times 10^3$ cells to $1 \times 10^7$ cells, $1 \times 10^4$ cells to $5 \times 10^6$ cells, $2 \times 10^4$ cells to $2 \times 10^6$ cells and $5 \times 10^4$ cells to $1 \times 10^6$ cells.

The Muse cells used in the cell preparation of the present invention have the property of accumulating at a site of myocardial infarction. Thus, in administering the cell preparation, there are no limitations on the administration site or type of vessel to which the cell preparation is administered (veins and arteries). Examples of veins suitable for administration include, but are not limited to, the ear vein and jugular vein. In the case of a human, the cubital vein is preferable. In addition, examples of arteries suitable for administration include, but are not limited to, a coronary artery. However, in consideration of such factors as cell transport efficiency and rapid recovery of the subject following surgery, the cell preparation is preferably administered directly into a coronary artery at an infarcted site by transdermal insertion of a cardiac catheter. Although there are no limitations on the puncture site of the cardiac catheter, examples thereof include the wrist (radial artery), elbow (brachial artery) and groin (femoral artery).

Although the cell preparation of the present invention is targeted for the treatment of serious massive myocardial infarction and other types of myocardial infarction, the time of administration is presumed to be a range extending from several hours to several weeks following ischemia. Thus, although there are no limitations thereon, the time of administration of the cell preparation of the present invention is preferably no later than within one month following ischemia. The time of administration is more preferably within 14 days, even more preferably within 7 days, still more preferably within 72 hours, even more preferably within 48 hours, even more preferably within 24 hours, still more preferably within 12 hours and most preferably within 6 hours following ischemia. Since the target of treatment using the cell preparation according to the present invention consists of cases in which the amount of time until reperfusion is extremely long or cases in which reperfusion and catheterization have been ineffective, it is extremely useful for treating myocardial infarction. In addition, since the Muse cells used have been confirmed in an experiment conducted by the inventors of the present invention to not induce an immune reaction even in the case of being derived from a allogenic source, there are no limitations on the number of administrations thereof, and may be suitably administered until the desired effect of treatment of myocardial infarction is obtained.

In an embodiment of the present invention, infarct size in a subject presenting with myocardial infarction can be reduced by administering the cell preparation of the present invention. Here, "infarct size" when used in the present description is defined as the ratio (%) of an infarcted region to an ischemic region. Here, an ischemic region is determined using Evan's blue staining, and non-ischemic regions are stained by this stain. On the other hand, an infarcted region is determined by triphenyl tetrazolium chloride (TTC) staining. Moreover, in the case of examining the effect of the cell preparation of the present invention on reducing infarct size, it is useful to use the reduction rate relative to the infarct size of a control (namely, (infarct size of control—infarct size following cell transplant)/infarct size of control×100). According to the present invention, infarct size is preferably reduced to 100% relative to a group not administered the cell preparation (control). Infarct size is more preferably reduced to 10% to 90%, even more preferably to 20% to 70%, and still more preferably to 30% to 50%. Furthermore, as indicated in Example 2 to be subsequently described, in the case of using a rabbit model of myocardial infarction, in contrast to infarct size having been an average of 30.4% in a control group, infarct size in a Muse cell transplant group was an average of 18.2%. On the basis of these values, infarct size can be understood to have been reduced by (30.4−18.2)/30.4×100= about 40% as a result of transplanting Muse cells.

In an embodiment of the present invention, the cell preparation of the present embodiment is able to improve cardiac function following myocardial infarction or restore to normal (or normal values). Improvement of cardiac function when used in the present description refers to alleviation and inhibition of the progression of various symptoms associated with myocardial infarction, and preferably refers to alleviation of symptoms to a degree that there is no impairment of daily life. In addition, restoring cardiac function to normal refers to all symptoms attributable to myocardial infarction returning to the state prior to myocardial infarction. Furthermore, in one mode of the present invention, the cell preparation of the present invention can be used to prevent and/or treat (chronic) heart failure following myocardial infarction.

Figure 6:
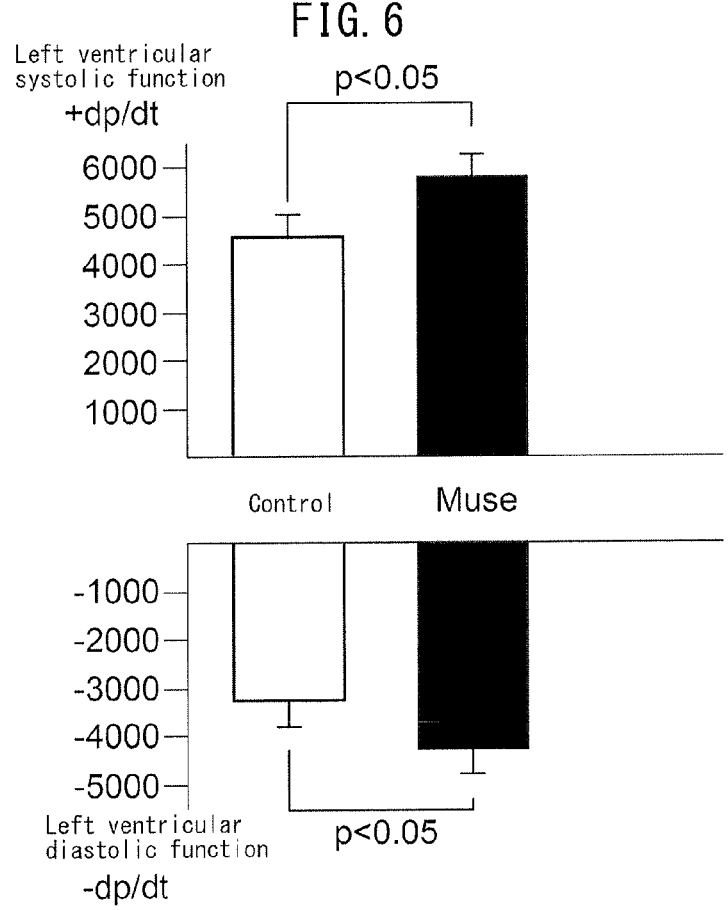
FIG. 6 indicates the results of examining cardiac function following Muse cell transplant using changes in blood pressure over time as an indicator (±dp/dt, p: blood pressure, t: time). The upper panel indicates the results of measuring ventricular systolic function (+dp/dt), while the lower panel indicates the results of measuring ventricular diastolic function (−dp/dt). These results suggest that cardiac function in a group of rabbits transplanted with Muse cells improved significantly in comparison with a control group.
Figure 7:
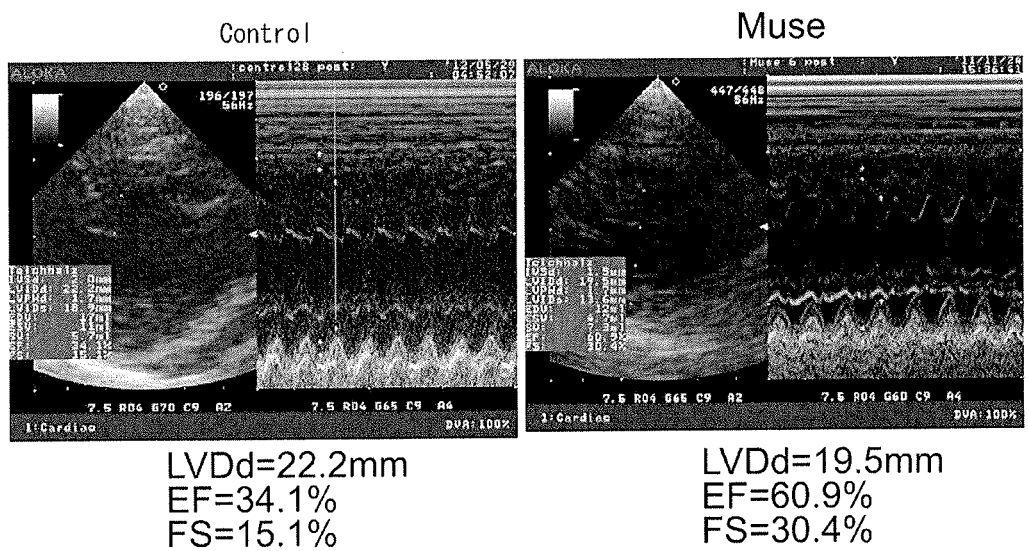
FIG. 7 depicts 2D echocardiograms of parasternal long axis cross-sections of the left ventricle. The left panel indicates an image of the left ventricle of a rabbit administered physiological saline (control), while the right panel indicates an image of the left ventricle of a rabbit transplanted with Muse cells. Indicators of cardiac function consisting of LVDd (left ventricular end-diastolic dimension), ejection fraction (EF) and left ventricular fractional shortening (FS) were measured based on these images. Each of these values was shown to be restored to normal in the Muse cell transplant group.
Figure 11:
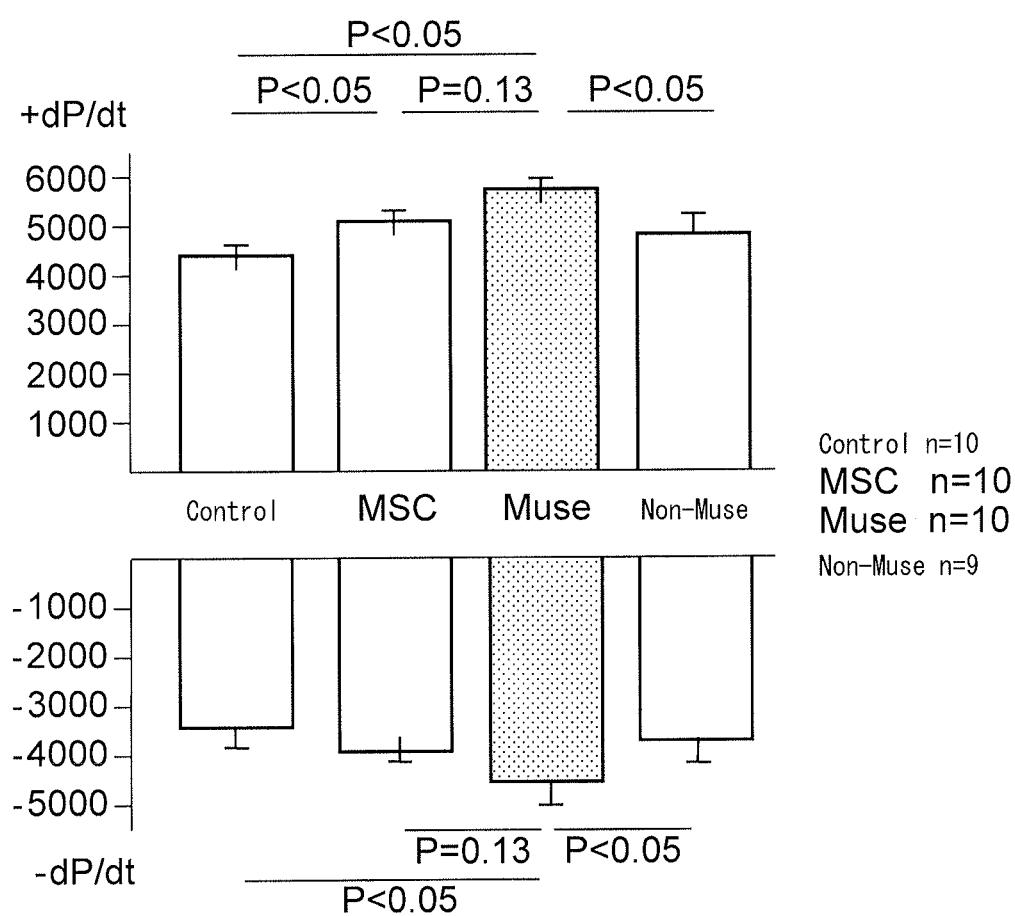
FIG. 11 indicates the results of examining cardiac function following Muse cell transplant using changes in blood pressure over time as an indicator (±dp/dt, p: blood pressure, t: time) in the same manner as FIG. 6. +dp/dt indicates systolic function while −dp/dt indicates diastolic function. These results suggest that cardiac function in a group of rabbits transplanted with Muse cells improved significantly in comparison with a control group, MSC transplant group and non-Muse cell transplant group.
Figure 12:
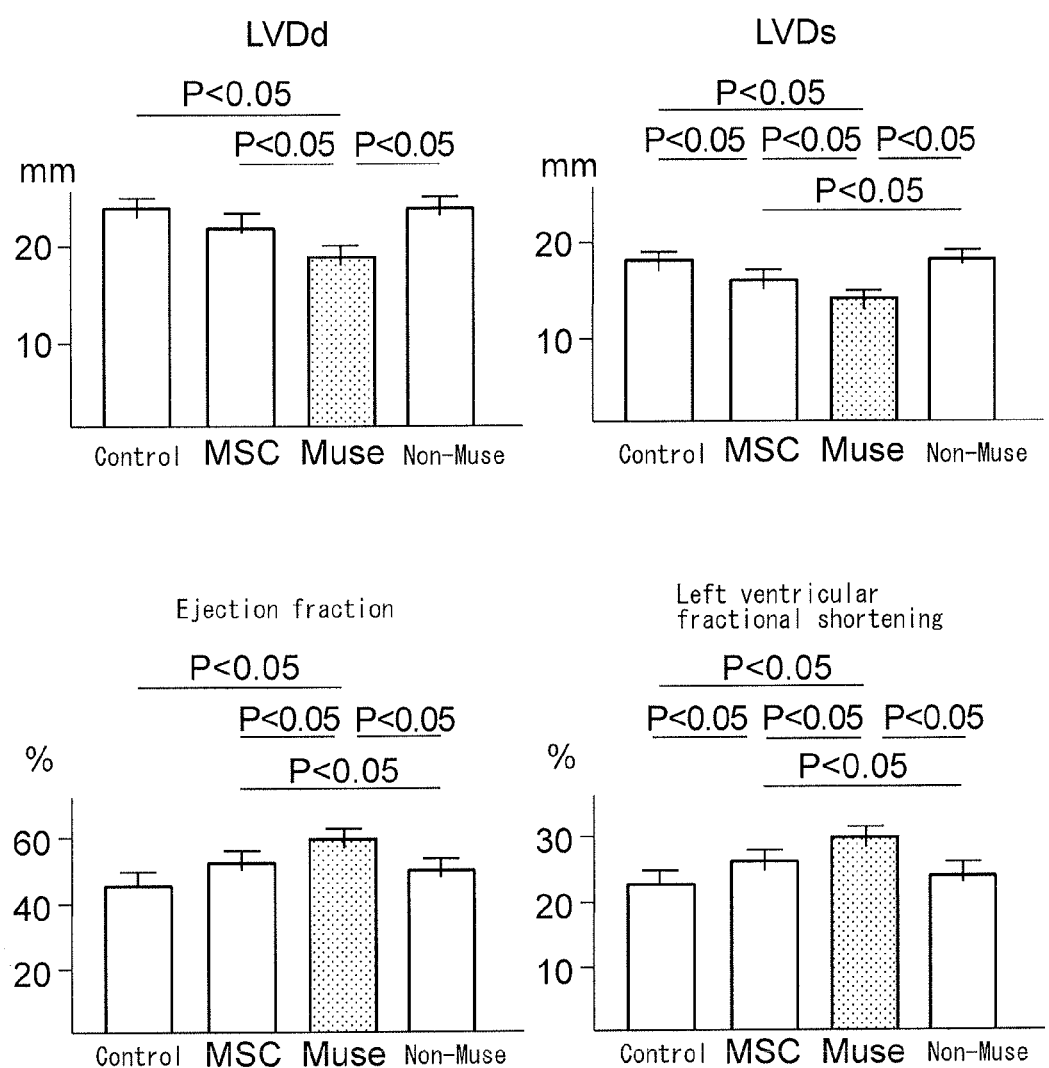
FIG. 12 indicates the results of measuring indicators of cardiac function consisting of LVDd (left ventricular end-diastolic dimension), left ventricular end-systolic dimension (LVDs), ejection fraction (EF) and left ventricular fractional shortening (FS) from 2D echocardiograms. Each of these values was shown to be restored to normal in the Muse cell transplant group.

Here, typical examples of indicators used to evaluate myocardial function include, but are not limited to, changes in blood pressure of the left ventricle over time (±dp/dt, p: blood pressure, t: time), left ventricular end-diastolic dimension (LVDd), ejection fraction (EF), left ventricular fractional shortening (FS) and left ventricular end-systolic dimension (LVDs). Improvement or restoration of cardiac function by the cell preparation of the present invention can be assessed using at least one of the aforementioned five indicators. For example, as described in Example 4, with respect to changes in blood pressure of the left ventricle over time (±dp/dt), although +dp/dt represents cardiac systolic function while −dp/dt represents cardiac diastolic function of the left ventricle, cardiac function was determined to be significantly improved in a cell transplant group in comparison with a control group based on both measured values (FIGS. 6 and 11). Moreover, with respect to LVDd, although an increase in LVDd was observed in a control group based on the results of 2D echocardiography, an increase in LVDd was not observed in a Muse cell transplant group and was within the normal range (FIGS. 7 and 12). Next, although ejection fraction (EF), which is one of the indicators of cardiac systolic function, is considered to be normal at a value of 55% or higher, since EF values were 60.9% (FIG. 7) and an average of 59.3% (n=10) (FIG. 12) in a Muse cell transplant group using a rabbit model of myocardial infarction, EF values were suggested to have returned to normal. In addition, with respect to left ventricular fractional shortening (FS) as well, which is also an indicator of cardiac systolic function in the same manner as EF, FS values were 30.4% (FIG. 7) and an average of 30.0% (n=10) (FIG. 12) in rabbits transplanted with Muse cells. Since the normal value for FS in humans is considered to be between 30% and 50%, FS values were suggested to have returned to normal with respect to this rabbit model of myocardial infarction as well.

Although the following provides a more detailed explanation of the present invention through examples thereof, the present invention is not limited in any way by these examples.

EXAMPLES

Example 1

Production of Rabbit Model of Myocardial Infarction

The protocol for experimentation using rabbits in the present example was approved by the ethics committee regarding animal experimentation of Gifu University, and was carried out in line with "Guidelines for the Care and Use of Laboratory Animals" (1996 revised edition) issued by the U.S. National Institutes of Health (NIH). More specifically, the procedure was as described below. First, Japanese white rabbits (body weight: approx. 2 to 3 kg/animal) were anesthetized using sodium pentobarbital at 30 mg/kg. The rabbits were continuously subjected to analysis of arterial blood gas, and ventilation conditions were suitably adjusted so that arterial blood gas was maintained within the physiological range. The left carotid artery and jugular vein were cannulated followed by monitoring of arterial pressure. After performing left thoracotomy at the third intercostal space, the heart was exposed and the center of the outer anterior surface of the left ventricle was ligated with 4-0 silk thread below a branch of the descending aorta. A narrow vinyl tube was passed over both ends of the suture thread, and the branch of the aorta was occluded by pulling on this suture thread. Next, the tube was fixed in position by clamping using mosquito hemostatic forceps. Myocardial ischemia was confirmed by the presence of local cyanosis and electrocardiogram changes. The duration of occlusion (ischemia) was suitably adjusted. After releasing the suture thread, cardiac muscle was confirmed to change to a red color throughout the entire critical area (refer to Yasuda, et al., Am. J. Physiol. Heart Circ. Physiol., 296, p. 1558-1565, 2009).

Example 2

Reduction Effect on Myocardial Infarct Size of Transplantation of Muse Cells (1) Preparation of Muse Cells Bone marrow cells were collected from rabbits (body weight: approx. 2 kg to 3 kg/animal) and SSEA-3-positive cells (Muse cells) were isolated using FACS. More specifically, Muse cells were isolated in compliance with the method described in International Publication No. WO 2011/007900 relating to isolation and identification of human Muse cells. Furthermore, the Muse cells used for transplant were derived from bone marrow cells of rabbit individuals in which myocardial infarction had been induced, adhesive mesenchymal cells were cultured from bone marrow, and lentivirus-GFP was introduced into the cells after allowing the cells to proliferate. Muse cells or a cell population containing Muse cells labeled with GFP were isolated with FACS to obtain cells double-positive for GFP and SSEA-3. Subsequently, the cells were adjusted to a prescribed concentration and returned to the same myocardial infarcted rabbit by intravenous injection. Furthermore, as was previously described, in the case of using cells obtained by culturing mesenchymal cells such as bone marrow cells as a parent population of Muse cells, all SSEA-3-positive cells are known to be positive for CD105 as reported by Wakao, et al. (2001, previously cited).

(2) Reduction Effect on Myocardial Infarct Size of Transplantation of Muse Cells The duration of infarction (ischemia) induced by ligation in the rabbits was made to be 30 minutes (corresponding to a duration of ischemia in humans of 3 hours), followed by initiating reperfusion by releasing the suture thread. SSEA-3-positive cells ($5 \times 10^5$ cells), for which concentration was adjusted with physiological saline after having been obtained as described in (1) above, were administered into an ear vein of the rabbits. In addition, a mesenchymal cell fraction (MSC) ($5 \times 10^5$ cells) and physiological saline were respectively administered into different rabbits for use as comparative controls followed by reperfusion. A comparative study of the reducing effect on infarct size of the Muse cells was then carried out 14 days after reperfusion.

More specifically, the rabbits were sacrificed 14 days after reperfusion by treating with heparin (500 U/kg) and intravenously injecting an excess amount of sodium pentobarbital. After excising the hearts of the animals, the infarcted regions of myocardial tissue were determined by staining with triphenyl tetrazolium chloride (TTC). Those regions that were not stained indicated infarcted sites. On the other hand, ischemic regions were determined by injecting Evan's blue stain (4%, Sigma Chemical Corp., St. Louis, Mo., USA) into the aortic artery at 80 mmHg. Tissue that has not become ischemic is stained blue by this stain, while ischemic regions appear white since this stain is not transported by capillaries.

The left ventricle was severed to obtain atrioventricular rings and a total of seven tissue sections were obtained. After weighing each tissue, the tissue sections were incubated in 1% TTC solution at 37° C. to visualize infarcted regions and capture images thereof (refer to Fishbein, et al., Am. Heart J., 101, 593-600, 1981). The results are shown in FIG. 1. In the figure, the left panel depicts an atrioventricular ring administered physiological saline for use as a control, while the right panel depicts an atrioventricular ring following transplantation of Muse cells. The regions in these tissue sections that are surrounded by broken lines (constituting a portion of cardiac muscle and papillary muscle) indicate infarcted regions that were not stained by TTC. Although infarcted regions similar to those present in the control were observed in the tissue section transplanted with Muse cells, those regions can be seen to be much narrower in comparison with the control.

Figure 2:
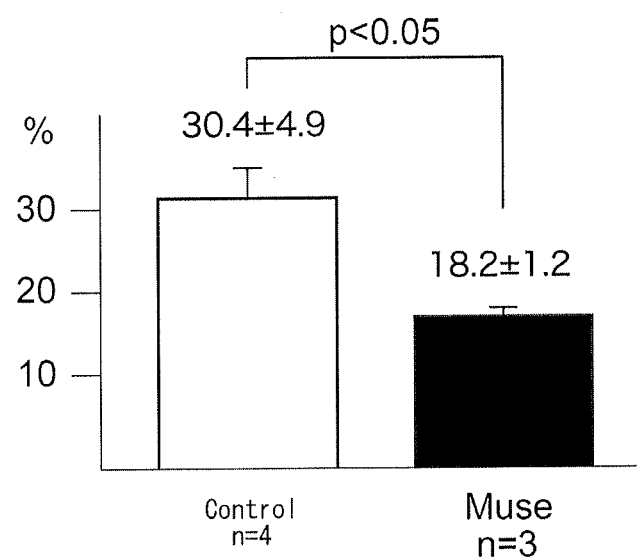
FIG. 2 is a bar graph depicting infarct size calculated as the ratio (%) of infarcted regions to ischemic regions following determination of infarcted sites by TTC staining. The left bar indicates the average value of infarct size for a physiological saline control group (n=3), while the right bar indicates the average value of infarct size in a Muse cell transplant group (n=4). Transplantation of Muse cells resulted in a significant decrease in infarct size.
Figure 8:
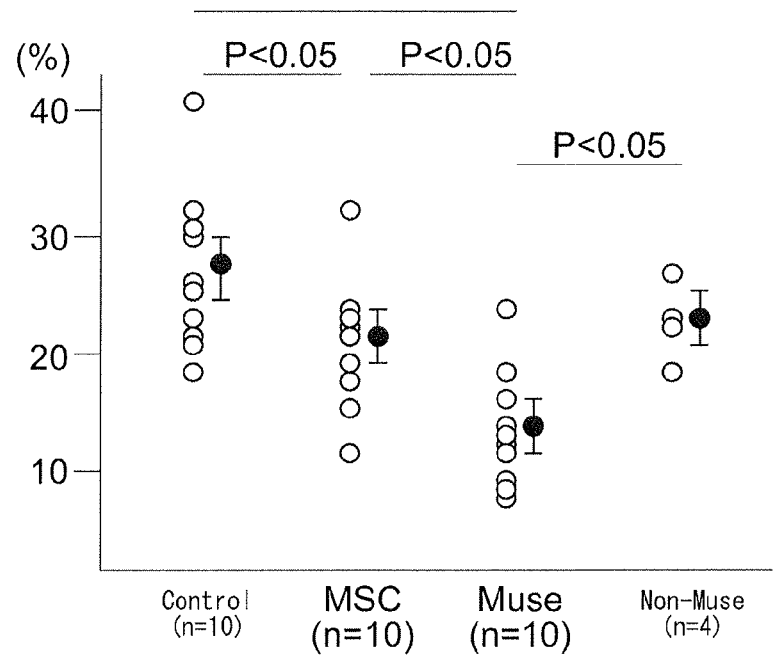
FIG. 8 is a graph depicting infarct size calculated as the ratio (%) of the infarcted region to the left ventricle following determination of infarcted sites by Masson's trichrome staining. Infarct size (white circles) and the average values thereof (black dots) of a physiological saline control group (n=10), an MSC (mesenchymal stem cell fraction) transplant group (n=10), a Muse cell transplant group (n=10), and a non-Muse cell group (MSC cells not including Muse cells) (n=4) are respectively plotted on the horizontal axis moving from left to right. Transplantation of Muse cells resulted in a significant reduction in infarct size in the same manner as in FIG. 2.

Moreover, infarct size was calculated as the ratio (%) of infarcted regions to ischemic regions (FIG. 2). Although infarct size was 30.4% in a control group (n=3), infarct size following transplantation of Muse cells (n=4) was 18.2%, thereby demonstrating that infarct size was significantly reduced by Muse cells. When this effect is calculated in terms of reduction rate, Muse cells were determined to be able to reduce infarct size by about 40%. Moreover, a similar test was carried out after increasing the number of specimens (FIG. 8). The average value of infarct size in a physiological saline control group (n=10) was 27.0%, that in an MSC cell (mesenchymal cell fraction) transplant group (n=10) was 21.0%, that in a Muse cell transplant group (n=10) was 13.9%, and that in a non-Muse cell (MSC cells not containing Muse cells) (n=4) was 22.8%. On the basis of these results as well, Muse cells were determined to have a considerable effect on reduction of infarct size.

Figure 3:
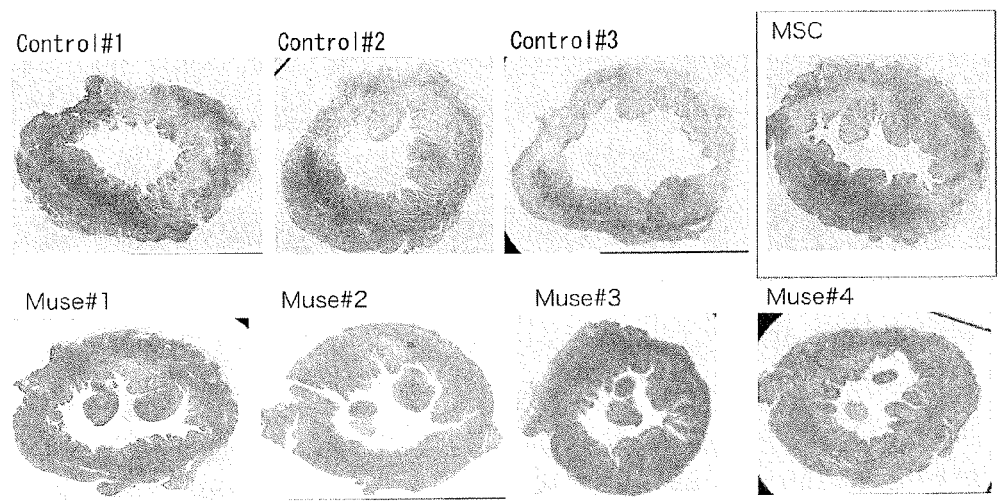
FIG. 3 shows the results of a histological examination of reduction effects on infarct size as determined by Masson's trichrome (MT) staining. In MT staining, tissue composed of viable cells is stained red, while tissue of infarcted regions exhibiting collagen fibrosis is not stained and appears pale. A Muse cell transplant group (n=4) demonstrated a smaller infarcted region and a considerable reduction in infarct size in comparison with a control group administered physiological saline (n=3). In addition, although reduction of infarct size was observed in tissue transplanted with a mesenchymal stem cell (MSC) fraction, reduction effects on infarct size were less potent in comparison with the Muse cell transplant group.
Figure 9:
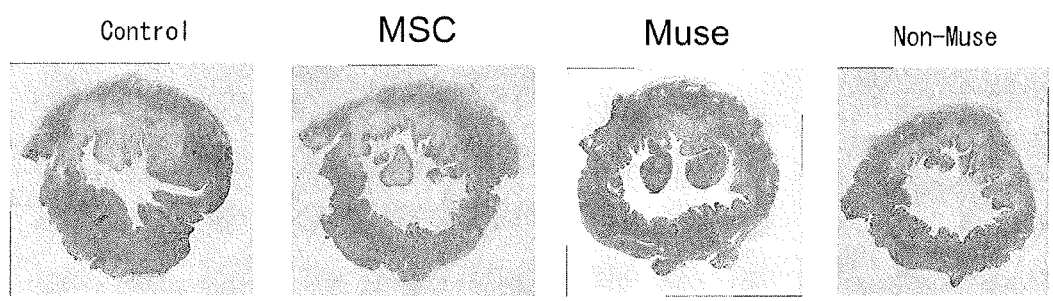
FIG. 9 shows the results of a histological examination of reduction effects on infarct size as determined by Masson's trichrome (MT) staining in the same manner as FIG. 3.

In addition, a histological examination was made of the reducing effect on infarct size by Masson's trichrome staining. After fixing hearts excised in the manner described above in 10% formalin and embedding in paraffin, sections were prepared in the direction of the horizontal cross-section from each specimen so as to obtain atrioventricular rings. Subsequently, the atrioventricular rings were stained with Masson's trichrome (MT) stain in accordance with ordinary methods to visualize infarcted regions of cardiac muscle (FIGS. 3 and 9). In the case of MT staining, tissue composed of viable cells is stained red, while tissue in which collagen fibrosis has progressed is pale and appears to have lost color. Tissue exhibiting collagen fibrosis that is not stained by MT (infarcted sites) covers a wide area in a control group administered physiological saline. On the other hand, in left ventricular tissue of a rabbit group transplanted with Muse cells, the pale areas were smaller than in the control group, demonstrating that infarct size has decreased. In addition, papillary muscle was also characteristically observed to have recovered from infarction. On the other hand, when left ventricle tissue of rabbits transplanted with MSC cells serving as a comparative control was compared with a control group administered physiological saline, although a reduction in infarct size was observed, the reducing effect on infarct size was less potent in comparison with that of the Muse cell transplant group. In addition, recovery of papillary muscle observed in the Muse cell transplant group was not observed in tissue transplanted with MSC cells.

Example 3

Differentiation of Muse Cells in Cardiac Tissue

Figure 4:
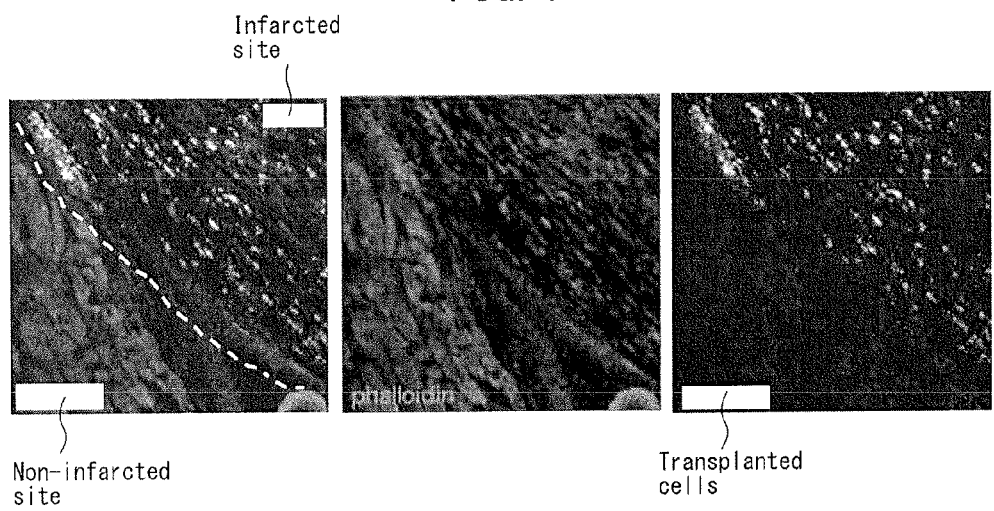
FIG. 4 depicts differentiation of Muse cells into myocardial cells in cardiac tissue. Infarcted sites and non-infarcted sites are distinguished with the broken line shown as a boundary line in the left panel. Myocardial cells were stained red by rhodamine-phalloidin staining (center panel). In addition, Muse cells preliminarily introduced with green fluorescent protein (GFP) gene prior to transplant using a lentivirus can be seen to be localized at infarcted sites (right panel). The result of superimposing these two images is shown in the left panel. As a result, a large number of cells where red and green colors overlap are present at the infarcted sites, thereby suggesting that transplanted Muse cells differentiate into myocardial cells.

A study was made as to whether or not the reduction of infarct size attributable to Muse cells observed in Example 2 was the result of differentiation by Muse cells into myocardial cells. First, Muse cells ($5 \times 10^5$), inserted with a gene so as to express green fluorescent protein (GFP), were injected into a rabbit model of myocardial infarction through an ear vein. Tissue sections were prepared in the same manner as Example 2 and the tissue was observed using fluorescent dyes for each type of tissue stain (FIG. 4). As is shown in the left panel of FIG. 4, the white broken line indicates a boundary line between an infarcted portion and a non-infarcted portion, with the portion above and to the right of the boundary line indicating infarcted sites and the portion below and to the left of the boundary line indicating non-infarcted sites. The center panel depicts the results of staining myocardial cells red with rhodamine-phalloidin stain in accordance with ordinary methods. This staining enables infarcted sites and non-infarcted sites to be clearly distinguished. In addition, the right panel indicates an image obtained from GFP staining, and Muse cells introduced with GFP gene (green) are indicated as having selectively accumulated at infracted sites. An image obtained by superimposing these two images is shown in the left panel. As a result, a large number of cells where red and green colors overlap are present at the infarcted sites, thereby suggesting that transplanted Muse cells differentiated into myocardial cells.

Figure 5:
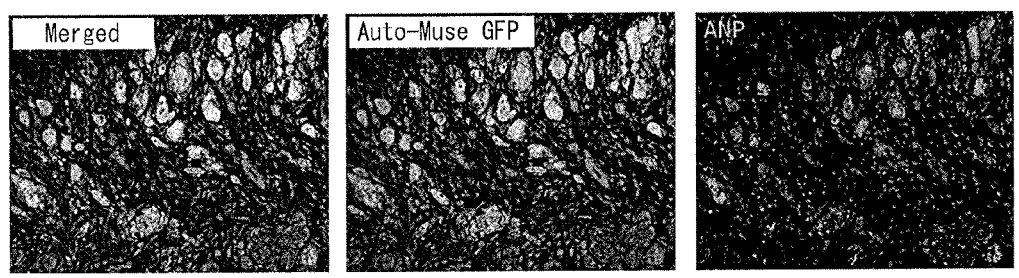
FIG. 5 shows the results of examining the differentiated state of Muse cells that have integrated into infarcted sites. The presence or absence of expression of atrial natriuretic peptide (ANP), which is known to be expressed in juvenile myocardial cells, was examined by fluorescent staining. The green color indicates GFP stain (Muse cells), the red color indicates ANP stain and the blue color indicates DAPI stain (which is used to stain cell nuclei). In the left panel, these three types of fluorescence are observed within a plurality of the same cells, thereby suggesting that cells are included among the transplanted Muse cells that are differentiating into myocardial cells.

Moreover, in order to investigate the differentiated state of GFP-positive Muse cells that integrated into infarcted sites, these cells were examined for the presence or absence of expression of atrial natriuretic peptide (ANP) in accordance with ordinary methods. This ANP is known to be expressed in juvenile myocardial cells. In FIG. 5, the green color indicates GFP stain (Muse cells), the red color indicates ANP stain and the blue color indicates DAPI stain (which is used to stain cell nuclei). As can be understood from the left panel of FIG. 5, since these three types of fluorescence were observed within a plurality of the same cells, transplanted Muse cells were suggested to include cells that were differentiating into myocardial cells.

Figure 10:
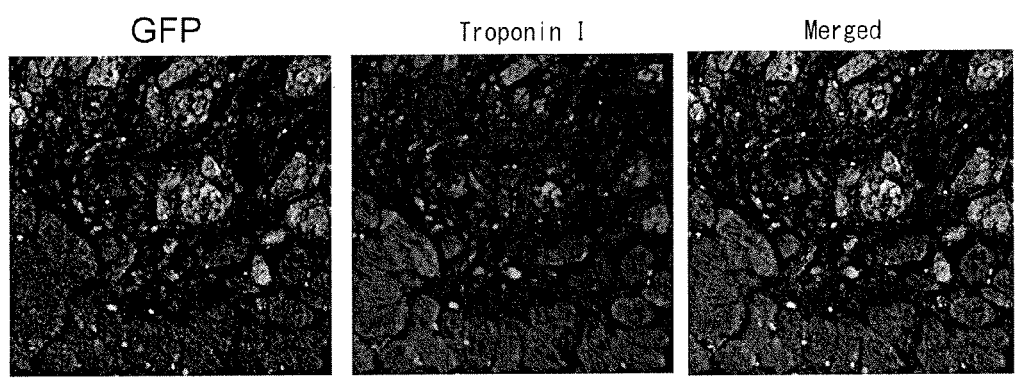
FIG. 10 shows the results of examining the differentiated state of Muse cells that have integrated into infarcted sites. The presence or absence of expression of troponin I, which is known to be a myocardial marker, was examined by fluorescent staining in the same manner as FIG. 4. The green color indicates GFP stain (Muse cells), the red color indicates troponin I stain and the blue color indicates DAPI stain (which is used to stain cell nuclei). In the left panel, these three types of fluorescence are observed within a plurality of the same cells, thereby suggesting that cells are included among the transplanted Muse cells that are differentiating into myocardial cells.

Next, an examination was made of the presence or absence of the expression of troponin I, which is known to be a myocardial marker, in GFP-positive Muse cells that integrated into infarcted sites. In troponin I staining, mouse anti-human troponin I antibody (Chemical International, Inc.), which cross-reacts with rabbit troponin I, was used as primary antibody. In FIG. 10, the green color indicates GFP stain (Muse cells), the red color indicates troponin I stain and the blue color indicates DAPI stain (which is used to stain cell nuclei). As can be understood from the right panel in FIG. 10, since these three types of fluorescence were observed within a plurality of the same cells, transplanted Muse cells were suggested to include cells that were differentiating into myocardial cells in the same manner as demonstrated by the aforementioned results (FIG. 5).

Figure 13:
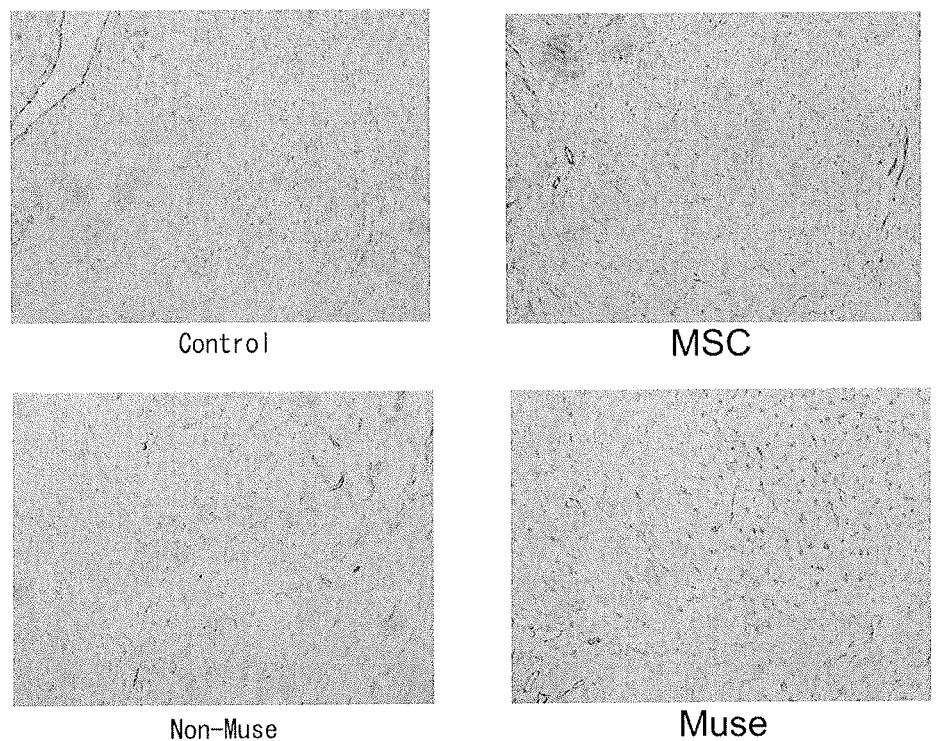
FIG. 13 shows the results of examining the differentiated state of Muse cells that have integrated into infarcted sites. The presence or absence of expression of CD31, which is known to be a vascular endothelial cell marker, was examined. Since CD31-positive microvascular density was high at infarcted sites of tissue transplanted with Muse cells in comparison with other transplant groups, the possibility is suggested that the transplant Muse cells differentiate into vascular endothelial cells. Microvascular density as observed in a high power field (HPF) is plotted on the vertical axis.
Figure 13:
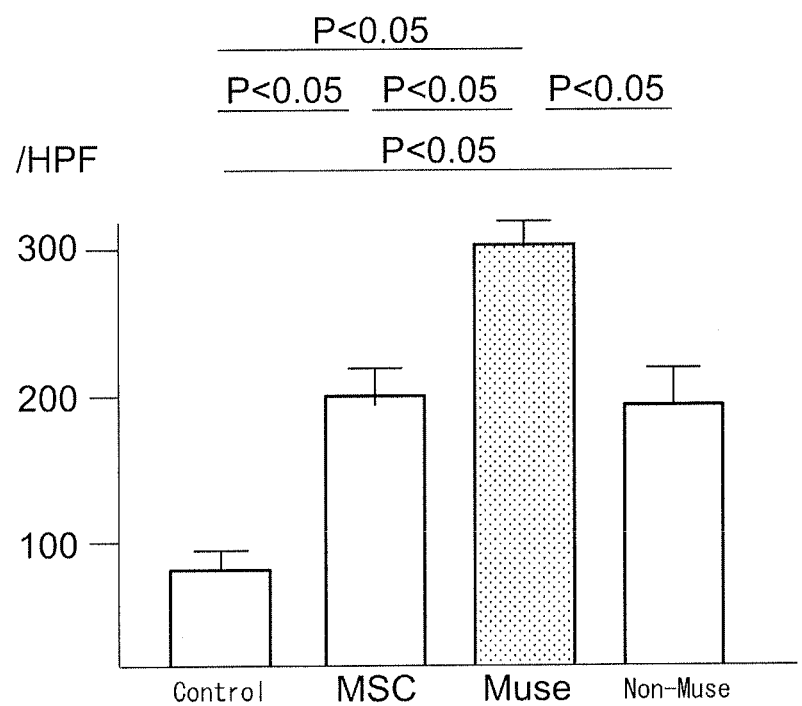

Moreover, an examination was made of the presence or absence of expression of CD31, which is known to be a vascular endothelial cell marker, in order to investigate the differentiated state of Muse cells that integrated into infarcted sites. More specifically, mouse anti-human CD31 monoclonal antibody (acquired from Dako Corp.), which cross-reacts with rabbit vascular endothelial cells, was used as primary antibody, and cells that expressed CD31 were histochemically stained. As is clear from the micrographs shown in FIG. 13, CD31-positive microvascular density at infarcted sites was higher in tissue transplanted with Muse cells than in the other transplant groups. On the basis thereof, the possibility was suggested that the transplanted Muse cells differentiate into vascular endothelial cells at infarcted sites.

Example 4

Evaluation of Improvement of Cardiac Function by Transplantation of Muse Cells

An examination was made of cardiac function following transplantation of Muse cells by using changes in blood pressure over time as an indicator (±dp/dt, p: blood pressure, t: time), and was assessed on the basis of images of cross-sections of the left ventricle obtained by 2D echocardiography. In these experiments, rabbits administered physiological saline 24 hours after reperfusion (control group, n=3) and a group of rabbits administered Muse cells (n=4) were used. First, measurement of changes in blood pressure over time was carried out by mildly anesthetizing each rabbit 14 days after reperfusion with 10 mg/kg of sodium pentobarbital, and inserting a catheter equipped with a micromanometer (SRP 407, Millar Instruments Inc.) into the left ventricle of the rabbits through the carotid artery. The values of +dp/dt, which represents cardiac systolic function of the left ventricle, and −dp/dt, which represents cardiac diastolic function of the left ventricle, that were obtained with this catheter were recorded. The results are shown in FIG. 6. Both cardiac systolic function (+dp/dt) (top of FIG. 6) and cardiac diastolic function (−dp/dt) (bottom of FIG. 6) demonstrated significant improvement of cardiac function in a group transplanted with Muse cells in comparison with a control group.

Moreover, the results of having examined cardiac function using changes in blood pressure over time in the same manner as previously described after increasing the number of specimens are shown in FIG. 11. Both cardiac systolic function (+dp/dt) (top of FIG. 11) and cardiac diastolic function (−dp/dt) (bottom of FIG. 11) demonstrated significant improvement of cardiac function in a rabbit group transplanted with Muse cells (n=10) in comparison with a control group (n=10), an MSC cell transplant group (n=10) and a non-Muse cell transplant group (n=9).

Next, 2D echocardiography was carried out in order to further confirm cardiac function in the aforementioned rabbits (control group and Muse cell transplant group). In this 2D echocardiography, images of the hearts of the rabbits were captured using an ultrasound diagnostic imaging system for use with animals (SSD2000, Aloka Corp.). Parasternal long axis cross-sections of the left ventricle obtained by measuring are shown in FIG. 7. The left panel indicates an image of the left ventricle of a control rabbit, while the right panel indicates an image of the left ventricle of a rabbit transplanted with Muse cells. The left ventricular end-diastolic dimension (LVDd) in the control was 22.2 mm. In contrast, since the value in the rabbit transplanted with Muse cells was smaller at 19.5 mm, infract size can be understood to have been reduced by Muse cells. Moreover, measurement of ejection fraction (EF), which is also used as an indicator of cardiac systolic function, yielded a value of 34.1% in the control, while the value in the rabbit transplanted with Muse cells was 60.9%. This ejection fraction is represented as the ratio of a single cardiac output of the left ventricle to left ventricular end-diastolic volume. Normally, an ejection volume of 55% or higher is considered to be normal in humans. Thus, the aforementioned measurement result suggests that cardiac function was returned to normal by transplantation of Muse cells in rabbits in comparison with the control. In addition, measurement of left ventricular fractional shortening (FS), which is also used as an indicator of cardiac systolic function in the same manner as EF, yielded a value of 15.1% in the control and value of 30.4% in the rabbit transplanted with Muse cells. This left ventricular fractional shortening is represented as a percentage by measuring left ventricular end-diastolic dimension and left ventricular end-systolic dimension using M-mode echocardiograms obtained by imaging, and dividing the difference thereof by the left ventricular end-diastolic dimension. Normally, the normal value in humans is considered to be within the range of 30% to 50%. Thus, the aforementioned measurement results suggest that cardiac function was returned to normal by transplantation of Muse cells in rabbits in comparison with the control.

In order to reconfirm the restoration of cardiac function to normal in rabbits following transplantation of Muse cells, LVDd, EF, FS (as previously described) and left ventricular end-systolic dimension (LVDs) were measured for control rabbits, rabbits transplanted with MSC cells and rabbits transplanted with non-Muse cells. Similar to the aforementioned results, LVDd, EF and FS all demonstrated that cardiac function was returned to normal in rabbits as a result of transplanting Muse cells. In addition, with respect to LVDs as well, in contrast to LVDs being an average of 18.3 mm in the control rabbits, the average value in rabbits transplanted with Muse cells was smaller at 13.8 mm, thereby suggesting that cardiac function was returned to normal as a result of transplanting Muse cells.

INDUSTRIAL APPLICABILITY

The cell preparation of the present invention is able to regenerate cardiac muscle at an infarcted site, reduce infarct size and improve cardiac function by administering transvenously into a cardiac infarction model, and can be applied to the treatment of myocardial infarction, and particularly serious massive myocardial infarction and heart failure associated therewith in humans.

All publications and patent documents cited in the present description are incorporated throughout the description by reference. Furthermore, although specific embodiments of the present invention have been explained in the present description for the purpose of exemplification, it can be easily understood by a person with ordinary skill in the art that the present invention may be modified in various ways without departing from the spirit and scope thereof.

The invention claimed is:

1. A method for treating a myocardial infarction in a subject in need thereof, the method comprising:
   administering to said subject a cell preparation containing a cell fraction comprising a population of pluripotent stem cells positive for SSEA-3, wherein the population of pluripotent stem cells is isolated from mesenchymal tissue or cultured mesenchymal cells by selecting for SSEA-3 positive cells, wherein the population of pluripotent stem cell is concentrated, wherein the pluripotent stem cells have a plurality of properties comprising:
   (i) CD105-positivity;
   (ii) low or absent telomerase activity;
   (iii) ability to differentiate into embryonic endoderm, ectoderm, and mesoderm germ layers; (iv) absence of neoplastic proliferation; and
   (v) ability to self-renew, and wherein the size of the myocardial infarction in the subject is reduced in comparison to a control subject that did not receive said cell preparation, thereby treating a myocardial infarction in a subject in need thereof.

2. The method according to claim 1, wherein the pluripotent stem cells positive for SSEA-3 have been concentrated by external stress stimulation.

3. The method according to claim 1, wherein the subject has heart failure following serious massive myocardial infarction and wherein the subject is a human.

4. The method according to claim 1, wherein the pluripotent stem cells are CD117-negative and CD146-negative.

5. The method according to claim 1, wherein the pluripotent stem cells are CD117-negative, CD146-negative, NG2-negative, CD34-negative, vWF-negative and CD271-negative.

6. The method according to claim 1, wherein the pluripotent stem cells are CD34-negative, CD117-negative, CD146-negative, CD271-negative, NG2-negative, vWF-negative, Sox10-negative, Snail-negative, Slug-negative, Tyrp1-negative and Dct-negative.

7. The method according to claim 1, wherein the pluripotent stem cells have the ability to integrate into the site of myocardial infarction.

8. The method according to claim 1, wherein the pluripotent stem cells have the ability to differentiate into myocardial cells.

9. The method according to claim 1, wherein the pluripotent stem cells have the ability to differentiate into vascular endothelial cells.

10. The method according to claim 1, wherein the cell preparation is administered into a vein or coronary artery of said subject within 1 month after said myocardial infarction one to ten times in a therapeutically effective amount of $1\times10^3$ cell to $1\times10^6$ cells.

11. The method according to claim 1, wherein at least one cardiac function indicator, selected from the group consisting of change in left ventricular pressure over time, left ventricular end-diastolic dimension (LVDd), ejection fraction (EF), left ventricular fractional shortening (FS) and left ventricular end-systolic dimension (LVDs), is restored to the value prior to myocardial infarction.

12. The method according to claim 1, wherein the cell preparation is administered into a vein or coronary artery of said subject within 1 month after said myocardial infarction in a therapeutically effective amount of $1.7 \times 10^5$ cells/kg body weight to $2.5 \times 10^5$ cells/kg body weight of the subject.

13. The method according to claim 2, wherein the external stress stimulation is a member selected from the group consisting of: protease treatment, culturing under phosphate-deficient conditions, culturing under serum-deficient conditions, culturing under nutrient-deficient conditions, culturing under exposure to heat shock, culturing under mechanical stimulation, culturing under shaking treatment, culturing under pressure treatment and physical shock, and a combination of a plurality thereof.

\* \* \* \* \*